(12) United States Patent
Ward et al.

(10) Patent No.: US 9,733,171 B2
(45) Date of Patent: Aug. 15, 2017

(54) ACOUSTIC CONCENTRATION OF PARTICLES IN FLUID FLOW

(75) Inventors: Michael W. Ward, Los Alamos, NM (US); Gregory Kaduchak, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 12/903,042

(22) Filed: Oct. 12, 2010

(65) Prior Publication Data

US 2011/0024335 A1 Feb. 3, 2011

Related U.S. Application Data

(63) Continuation of application No. 11/784,936, filed on Apr. 9, 2007, now Pat. No. 7,837,040.

(51) Int. Cl.
*B07C 5/00* (2006.01)
*G01N 1/40* (2006.01)
*C12M 1/00* (2006.01)

(52) U.S. Cl.
CPC .......... *G01N 1/4077* (2013.01); *C12M 47/02* (2013.01); *G01N 2001/4094* (2013.01)

(58) Field of Classification Search
CPC ......... G01N 1/4077; G01N 2001/4094; G01N 1/40; C02F 1/36; B07B 2230/04; B01D 11/0261; B01D 2273/24
USPC ..................... 209/18, 210, 156, 590; 210/748
See application file for complete search history.

(56) References Cited

U.S. PATENT DOCUMENTS

| 2,900,536 | A | 8/1959 | Palo |
| 3,669,542 | A | 6/1972 | Capellaro |
| 3,882,732 | A | 5/1975 | Fletcher et al. |
| 4,055,491 | A | 10/1977 | Porath-Furedi |
| 4,265,124 | A | 5/1981 | Lim et al. |
| 4,285,810 | A | 8/1981 | Kirkland et al. |
| 4,350,683 | A | 9/1982 | Galfre et al. |

(Continued)

FOREIGN PATENT DOCUMENTS

| CN | 1493831 A | 5/2004 |
| CN | 1524948 | 9/2004 |

(Continued)

OTHER PUBLICATIONS

Benes, "Separation of Dispersed Particles by Ultrasonic-Induced Coagulation", 15th Conference of the German Society for Acoustics, 1989, 2 pages.

(Continued)

*Primary Examiner* — Joseph C Rodriguez
*Assistant Examiner* — Kalyanavenkateshware Kumar
(74) *Attorney, Agent, or Firm* — Baker & Hostetler LLP (57) ABSTRACT

Disclosed herein is a acoustic concentration of particles in a fluid flow that includes a substantially acoustically transparent membrane and a vibration generator that define a fluid flow path therebetween. The fluid flow path is in fluid communication with a fluid source and a fluid outlet and the vibration generator is disposed adjacent the fluid flow path and is capable of producing an acoustic field in the fluid flow path. The acoustic field produces at least one pressure minima in the fluid flow path at a predetermined location within the fluid flow path and forces predetermined particles in the fluid flow path to the at least one pressure minima.

20 Claims, 4 Drawing Sheets

(56) References Cited

U.S. PATENT DOCUMENTS

| | | | |
|---|---|---|---|
| 4,434,230 A | 2/1984 | Ritts, Jr. | |
| 4,492,752 A | 1/1985 | Hoffman et al. | |
| 4,503,385 A | 3/1985 | Haynes | |
| 4,523,682 A | 6/1985 | Barmatz et al. | |
| 4,523,982 A | 6/1985 | Lee | |
| 4,596,464 A | 6/1986 | Hoffman et al. | |
| 4,604,542 A | 8/1986 | Thompson | |
| 4,673,512 A | 6/1987 | Schram | |
| 4,743,361 A | 5/1988 | Schram | |
| 4,759,775 A | 7/1988 | Peterson et al. | |
| 4,777,823 A | 10/1988 | Barmatz et al. | |
| 4,790,653 A | 12/1988 | North, Jr. | |
| 4,845,025 A | 7/1989 | Lary et al. | |
| 4,867,559 A | 9/1989 | Bach | |
| 4,877,516 A | 10/1989 | Schram | |
| 4,913,883 A | 4/1990 | Imai et al. | |
| 4,964,303 A | 10/1990 | Barmatz et al. | |
| 4,979,824 A | 12/1990 | Mathies et al. | |
| 4,987,086 A | 1/1991 | Brosnan et al. | |
| 4,991,923 A | 2/1991 | Kino et al. | |
| 5,006,266 A | 4/1991 | Schram | |
| 5,030,002 A | 7/1991 | North, Jr. | |
| 5,032,381 A | 7/1991 | Bronstein et al. | |
| 5,040,890 A | 8/1991 | North, Jr. | |
| 5,079,959 A | 1/1992 | Miyake et al. | |
| 5,085,783 A | 2/1992 | Feke et al. | |
| 5,106,187 A | 4/1992 | Bezanson | |
| 5,164,094 A | 11/1992 | Stuckart | |
| 5,225,089 A | 7/1993 | Benes et al. | |
| 5,245,318 A | 9/1993 | Tohge | |
| 5,264,906 A | 11/1993 | Ferer et al. | |
| 5,346,670 A | 9/1994 | Renzoni et al. | |
| 5,376,551 A | 12/1994 | Yoshikami | |
| 5,395,588 A | 3/1995 | North, Jr. et al. | |
| 5,430,541 A | 7/1995 | Sapp | |
| 5,491,344 A | 2/1996 | Kenny et al. | |
| 5,504,337 A | 4/1996 | Lakowicz et al. | |
| 5,517,870 A | 5/1996 | Kurimura | |
| 5,527,460 A | 6/1996 | Trampler et al. | |
| 5,528,045 A | 6/1996 | Hoffman et al. | |
| 5,547,849 A | 8/1996 | Baer et al. | |
| 5,626,767 A * | 5/1997 | Trampler et al. | 210/748.05 |
| 5,644,388 A | 7/1997 | Maekawa et al. | |
| 5,674,698 A | 10/1997 | Zarling et al. | |
| 5,688,406 A | 11/1997 | Dickinson et al. | |
| 5,690,895 A * | 11/1997 | Matsumoto et al. | 422/73 |
| 5,711,888 A | 1/1998 | Trampler et al. | |
| 5,739,902 A | 4/1998 | Gjelsnes et al. | |
| 5,798,222 A | 8/1998 | Goix | |
| 5,800,861 A | 9/1998 | Chiang et al. | |
| 5,831,166 A | 11/1998 | Kozuka et al. | |
| 5,915,925 A | 6/1999 | North | |
| 5,981,180 A | 11/1999 | Chandler et al. | |
| 5,999,256 A | 12/1999 | Jones et al. | |
| 6,003,388 A | 12/1999 | Oeftering | |
| 6,048,444 A | 4/2000 | Takahashi | |
| 6,055,859 A | 5/2000 | Kozuka et al. | |
| 6,074,879 A | 6/2000 | Zelmanovic et al. | |
| 6,090,295 A | 7/2000 | Raghavarae et al. | |
| 6,161,435 A * | 12/2000 | Bond et al. | 73/587 |
| 6,197,593 B1 * | 3/2001 | Deka et al. | 436/63 |
| 6,216,538 B1 | 4/2001 | Yasuda et al. | |
| 6,221,258 B1 | 4/2001 | Feke et al. | |
| 6,228,652 B1 | 5/2001 | Rodriguez et al. | |
| 6,248,590 B1 | 6/2001 | Malachowski | |
| 6,255,118 B1 | 7/2001 | Alfano et al. | |
| 6,309,886 B1 | 10/2001 | Ambrose et al. | |
| 6,332,541 B1 | 12/2001 | Coakley et al. | |
| 6,348,687 B1 | 2/2002 | Brockmann et al. | |
| 6,373,567 B1 | 4/2002 | Wise et al. | |
| 6,449,563 B1 | 9/2002 | Dukhin et al. | |
| 6,467,350 B1 | 10/2002 | Kaduchak et al. | |
| 6,532,061 B2 | 3/2003 | Ortyn et al. | |
| 6,549,275 B1 | 4/2003 | Cabuz et al. | |
| 6,565,727 B1 | 5/2003 | Shenderov et al. | |
| 6,592,821 B1 | 7/2003 | Wada et al. | |
| 6,604,435 B2 | 8/2003 | Buchanan et al. | |
| 6,644,118 B2 | 11/2003 | Kaduchak et al. | |
| 6,647,739 B1 | 11/2003 | Kim et al. | |
| 6,668,664 B1 | 12/2003 | Ohkawa | |
| 6,683,314 B2 | 1/2004 | Oostman, Jr. et al. | |
| 6,713,019 B2 | 3/2004 | Ozasa et al. | |
| 6,736,904 B2 | 5/2004 | Poniatowski et al. | |
| 6,773,556 B1 | 8/2004 | Brockie et al. | |
| 6,794,671 B2 | 9/2004 | Nicoli et al. | |
| 6,797,158 B2 | 9/2004 | Feke et al. | |
| 6,813,017 B1 | 11/2004 | Hoffman et al. | |
| 6,816,257 B2 | 11/2004 | Goix | |
| 6,831,279 B2 | 12/2004 | Ho | |
| 6,881,314 B1 | 4/2005 | Wang et al. | |
| 6,911,082 B2 | 6/2005 | Sato et al. | |
| 6,929,750 B2 | 8/2005 | Laurell et al. | |
| 6,949,355 B2 | 9/2005 | Yamanishi et al. | |
| 6,982,165 B2 | 1/2006 | Yamakawa et al. | |
| 7,008,540 B1 | 3/2006 | Weavers et al. | |
| 7,018,819 B2 | 3/2006 | Orwar et al. | |
| 7,047,809 B2 | 5/2006 | Cobb | |
| 7,052,864 B2 | 5/2006 | Durkop et al. | |
| 7,064,823 B2 | 6/2006 | Roche et al. | |
| 7,081,192 B1 | 7/2006 | Wang et al. | |
| 7,091,348 B2 | 8/2006 | O'Neill et al. | |
| 7,108,137 B2 | 9/2006 | Lal et al. | |
| 7,113,266 B1 | 9/2006 | Wells | |
| 7,161,665 B2 | 1/2007 | Johnson | |
| 7,166,443 B2 | 1/2007 | Walker et al. | |
| 7,255,780 B2 | 8/2007 | Shenderov | |
| 7,262,838 B2 | 8/2007 | Fritz | |
| 7,315,357 B2 | 1/2008 | Ortyn et al. | |
| 7,329,545 B2 | 2/2008 | Pamula et al. | |
| 7,340,957 B2 | 3/2008 | Kaduchak et al. | |
| 7,362,432 B2 | 4/2008 | Roth | |
| 7,373,805 B2 | 5/2008 | Hawkes et al. | |
| 7,403,125 B2 | 7/2008 | Rich | |
| 7,431,892 B2 | 10/2008 | Zumeris et al. | |
| 7,477,363 B2 | 1/2009 | Nagai | |
| 7,570,676 B2 | 8/2009 | Essaian et al. | |
| 7,758,811 B2 | 7/2010 | Durack et al. | |
| 7,990,525 B2 | 8/2011 | Kanda | |
| 2003/0059850 A1 | 3/2003 | Evans | |
| 2003/0086608 A1 | 5/2003 | Frost et al. | |
| 2003/0098421 A1 | 5/2003 | Ho | |
| 2003/0235919 A1 | 12/2003 | Chandler | |
| 2004/0065599 A1 | 4/2004 | Lal et al. | |
| 2005/0072677 A1 | 4/2005 | Gascoyne et al. | |
| 2005/0097968 A1 | 5/2005 | Ishikawa et al. | |
| 2006/0006769 A1 | 1/2006 | Masters et al. | |
| 2006/0021437 A1 | 2/2006 | Kaduchak et al. | |
| 2006/0034733 A1 | 2/2006 | Ferren et al. | |
| 2006/0071580 A1 | 4/2006 | Sawada | |
| 2006/0163166 A1 | 7/2006 | Hawkes et al. | |
| 2007/0037172 A1 * | 2/2007 | Chiu et al. | 435/6 |
| 2007/0071683 A1 | 3/2007 | Dayton et al. | |
| 2007/0098232 A1 | 5/2007 | Matula et al. | |
| 2007/0119239 A1 | 5/2007 | Priev et al. | |
| 2007/0159627 A1 | 7/2007 | Johnson | |
| 2007/0177146 A1 | 8/2007 | Fujimoto | |
| 2007/0236681 A1 | 10/2007 | Ilkov | |
| 2008/0053787 A1 * | 3/2008 | Bagajewicz | 196/111 |
| 2008/0106736 A1 | 5/2008 | Graves et al. | |
| 2008/0245709 A1 | 10/2008 | Kaduchak et al. | |
| 2008/0245745 A1 | 10/2008 | Ward et al. | |
| 2009/0029870 A1 | 1/2009 | Ward et al. | |
| 2009/0038932 A1 | 2/2009 | Denslow et al. | |
| 2009/0042239 A1 | 2/2009 | Ward et al. | |
| 2009/0042310 A1 | 2/2009 | Ward et al. | |
| 2009/0045107 A1 | 2/2009 | Ward et al. | |
| 2009/0048805 A1 | 2/2009 | Kaduchak et al. | |
| 2009/0050573 A1 | 2/2009 | Ward et al. | |
| 2009/0053686 A1 | 2/2009 | Ward et al. | |
| 2009/0107241 A1 | 4/2009 | Goddard et al. | |
| 2009/0139332 A1 | 6/2009 | Goddard et al. | |
| 2009/0158823 A1 | 6/2009 | Kaduchak et al. | |
| 2009/0162887 A1 | 6/2009 | Kaduchak et al. | |
| 2009/0178716 A1 | 7/2009 | Kaduchak et al. | |

(56) References Cited

U.S. PATENT DOCUMENTS

| | | | |
|---|---|---|---|
| 2009/0227042 | A1 | 9/2009 | Gauer et al. |
| 2009/0316151 | A1 | 12/2009 | Matula et al. |
| 2010/0000325 | A1 | 1/2010 | Kaduchak et al. |
| 2010/0009333 | A1 | 1/2010 | Auer |
| 2011/0032522 | A1 | 2/2011 | Graves et al. |
| 2011/0134426 | A1 | 6/2011 | Kaduchak et al. |

FOREIGN PATENT DOCUMENTS

| | | |
|---|---|---|
| CN | 1739020 A | 2/2006 |
| CN | 101060898 | 10/2007 |
| DE | 3027433 | 2/1982 |
| EP | 0 147 032 | 3/1985 |
| EP | 0 292 470 | 11/1988 |
| EP | 0 773 055 | 5/1997 |
| EP | 1 416 239 | 5/2004 |
| FR | 821419 | 12/1937 |
| GB | 500271 | 12/1937 |
| JP | 363139231 | 6/1988 |
| JP | 01-112161 | 4/1989 |
| JP | 406241977 | 9/1994 |
| JP | 07-047259 | 2/1995 |
| JP | 408266891 | 10/1996 |
| JP | 11-014533 | 1/1999 |
| JP | 2002-22531 | 1/2002 |
| RU | 2224992 | 2/2004 |
| WO | WO 88/09210 | 12/1988 |
| WO | WO 90/05008 | 5/1990 |
| WO | WO 94/29695 | 12/1994 |
| WO | WO 97/02482 | 1/1997 |
| WO | WO 99/42810 | 8/1999 |
| WO | WO 00/41794 | 7/2000 |
| WO | WO 02/059577 | 8/2002 |
| WO | WO 02/072234 | 9/2002 |
| WO | WO 02/072236 | 9/2002 |
| WO | WO 03/079006 | 9/2003 |
| WO | WO 2004/024287 | 3/2004 |
| WO | WO 2004/033087 | 4/2004 |
| WO | WO 2004/048948 | 6/2004 |
| WO | WO 2006/031299 | 3/2006 |
| WO | WO 2006/032703 | 3/2006 |
| WO | WO 2006/076195 | 7/2006 |
| WO | WO 2007/128795 | 11/2007 |
| WO | WO 2008/122051 | 10/2008 |
| WO | WO 2009/086043 | 7/2009 |
| WO | WO 2009/091925 | 7/2009 |
| WO | WO 2011/068764 | 6/2011 |

OTHER PUBLICATIONS

Groschl, "Automatic frequency control for piezoelectric resonators and their implementation in the acoustic driftwave resonator", Thesis implemented at the Institute for General Physics the Technical University of Vienna, Nov. 1991, 2 pages.
Petersson et al., "Separation of Lipids from Blood Utilizing Ultrasonic Standing Waves in Microfluidic Channels," *Analyst*, 2004, 129, 938-943.
Response to Mar. 24, 2010 Extended European Search Report in European Application No. 08733084.1 filed Jun. 16, 2010.
International Application No. PCT/US05/26524: International Search Report dated Oct. 3, 2006.
International Application No. PCT/US08/87579, Written Opinion dated Feb. 9, 2009.
U.S. Appl. No. 11/982,042: Final Office Action dated Sep. 24, 2010.
U.S. Appl. No. 11/982,042: Non-Final Office Action dated Mar. 4, 2011.
U.S. Appl. No. 11/593,312: Non-Final Office Action dated Oct. 16, 2008.
U.S. Appl. No. 11/593,312: Final Office Action dated May 13, 2009.
U.S. Appl. No. 11/593,312: Non-Final Office Action dated Oct. 23, 2009.
U.S. Appl. No. 11/593,312: Final Rejection dated Apr. 5, 2010.
U.S. Appl. No. 11/593,312: Notice of Allowance dated Jul. 6, 2010.
U.S. Appl. No. 11/593,312: Notice of Allowance dated Sep. 16, 2010.
U.S. Appl. No. 11/784,928: Notice of Allowance dated Dec. 13, 2010.
U.S. Appl. No. 11/784,936: Notice of Allowance dated May 28, 2010.
U.S. Appl. No. 11/784,936: Notice of Allowance dated Sep. 16, 2010.
U.S. Appl. No. 12/283,491: Restriction Requirement dated Jun. 25, 2010.
U.S. Appl. No. 12/283,491: Non-Final Office Action dated Sep. 27, 2010.
U.S. Appl. No. 12/283,491: Final Office Action dated Apr. 5, 2011.
U.S. Appl. No. 12/283,461: Restriction Requirement dated Jun. 28, 2010.
U.S. Appl. No. 12/283,461: Non-Final Office Action dated Sep. 28, 2010.
U.S. Appl. No. 12/283,461: Final Office Action dated Apr. 5, 2011.
U.S. Appl. No. 12/903,003: Non-Final Office Action dated Nov. 15, 2010.
U.S. Appl. No. 12/903,003: Final Office Action dated Jun. 23, 2011.
Aboobaker, N. et al., "Mathematical modeling of the movement of suspended particles subjected to acoustic and flow fields", App. Math. Modeling, 2005, 29, 515-532.
Aleksandrov, et al., "Pulsed Laser Florescence Spectrometer," Zhurnal Prikladnoi Spektroskopii 47(4), Oct. 1987, pp. 686-692.
Anderson, M. et al., "The Physics and Technology of Ultrasonic Particle Separation in Air", WCU, 2003, 1615-1621.
Apfel, R.E. et al., "Acoustic Radiation Pressure—Principles and Application to Separation Science", Fortschritte Der Akustik DAGA '90, 1990, 19-30.
Araz, M.K. et al., "Ultrasonic Separation in Microfluidic Capillaries", IEEE Ultrasonics Symposium, 2003, 1066-1069.
Asai, K. et al., "Ultrasonic treatment of slurry", Third International Coal Preparation Conference, 1958, 518-527.
Bardsley, et al., "Electroacoustic Productions of Murine Hybridomas," Journal of Immunological Methods, 129(1), (no month available) 1990, pp. 41-47.
Barmatz, M. et al., "Acosutic radiation potential on a sphere in plane, cylindrical, and spherical standing wave fields", J. Acoust. Soc. Am., 1985, 77, 928-945.
Bauerecker, S. et al., "Formation and growth of ice particles in stationary ultrasonic fields", J. of Chem. Phys., 1998, 3709-3712.
Bazou, D. et al., "Physical Environment of 2-D Animal Cell Aggregates Formed in a Short Pathlength Ultrasound Standing Wave Trap", Ultrasound in Med. & Biol., 2005, 31, 423-430.
Benes, E. et al., "Abscheidung Dispergierter Teilchen Durch Ultraschall-Induzierte Koagulation", Taauna der Deutschen Arbeitsaameinschaft fur Akustik—DAGA '89, 1989, 1-4.
Benes, E. et al., "Improved quartz crystal microbalance technique", J. Appl. Phys., 1984, 56, 608-626.
Beverloo, H.B. et al., "Inorganic Phsophors as New Luminescent Labels for Irnmunocytochernistry and Time-Resolved Microscopy", Cytometry, 1990, 11, 784-792.
Bienvenue, J.M. et al., "Microchip-Based Cell Lysis and DNA Extraction from Sperm Cells for Application to Forensic Analysis", J. Forensic Sci., 2006, 51, 266-273.
Binks, B.P. et al., "Modern Aspects of Emulsion Science", The Royal Society of Chemistry, 1998, 310-321.
Bishop, J.E. et al., "Mechanism of higher brightness of PerCP-Cy5. 5", Cytometry Supp, 2000, 10, 162-163.
Borgnis, "Acoustic Radiation Pressure of Plane Compressional Waves," Reviews of Modern Physics 25( 3), Jul. 1953, pp. 653-664.
Borisov, S.M. et al., "Blue LED Excitable Temperature Sensors Based ona New Eurpium (III) Chelate," J. Fluoresc., 2008, 18,581-589.
Borthwick, K.A. et al., "Development of a novel compact sonicator for cell disruption", J. of Microbioloaical Methods, 2005, 60, 207-216.
Bosma, R. et al., "Ultrasound, a new separation technique to harvest microalgae", J. Appl. Phycology, 2003, 15, 143-153.

(56) References Cited

OTHER PUBLICATIONS

Bossuyt, X. et al., "Comparative Analysis for Whole Blood Lysis Methods for Flow Cytometry", Cytometry, 1997, 30, 124-133.
Brodeur, P. H., "Acoustic Separation in a Laminar Flow," Ultrasonics Symposium, 1994, pp. 1359-1362.
Caperan, P.H. et al., "Acoustic Agglomeration of a Glycol Fog Aerosol: Influence of Particle Concentration and Intensity of the Sound Field at Two Frequencies", J. Aerosol Sci., 1995, 26, 595-612.
Chase, E.S. et al., "Resolution of Dimly Fluorescent Particles: A Practical Measure of Fluorescence Sensitivity", Cytometry, 1998, 33, 267-279.
Cheung, et al., "Impedance Spectroscopy Flow Cytometry: On-Chip Label-Free Cell Differentiation," Cytometry Part A 65A, Feb. 10, 2005, pp. 124-132.
Coakley, W.T. et al., "Analytical scale ultrasonic standing wave manipulation of cells and microparticles", Ultrasonics, 2000, 38, 638-641.
Coakley, W.T. et al., "Cell-cell contact and membrane spreading in an ultrasound trap", Colloids and Surfaces B: Biointerfaces, 2004, 34, 221-230.
Coakley, W.T. et al., "Ultrasonic separations in analytical biotechnology", Tibtech, 1997, 15, 506-511.
Condrau, M.A. et al., "Time-Resolved Flow Cytometry for the Measurement of Lanthanide Chelate Fluorescence: I. Concept and Theoretical Evaluation", Cytometry, 1994, 16, 187-194.
Condrau, M.A. et al., "Time-Resolved Flow Cytometry for the Measurement of Lanthanide Chelate Fluorescence: II. Instrument Design and Experimental Results", Cytometry, 1994, 16, 195-205.
Cousins, C.M. et al., "Plasma Preparation from Whole Blood Using Ultrasound", Ultrasound in Med. & Biol., 2000, 26, 881-888.
Curtis, H.W. et al., "Ultrasonic Continuous Flow Plasmapheresis Separator", IBM Tech. Disc. Bulletin, 1982, 25,192-1 93.
Czyz, H. et al., "On the Concentration of Aerosol Particles by Means of Drift Forces in a Standing Wave Field", Acustica, 1990, 70, 23-28.
Dain, Y. et al., "Dynamics of Suspended Particles in a Two-Dimensional High-Frequency Sonic Field", J. Aerosol Sci., 1995, 26, 575-594.
Dain, Y. et al., "Side drift of aerosols in two-dimensional resonant acoustic levitators", J. Acoust. Soc. Am, 1997, 102, 2549-2555.
Danilov, S D. et al., "Mean force on a small sphere in a sound field in a viscous fluid", J. Acoust. Soc. Am., 2000, 107, 143-1 53.
Danilov, S.D. et al., "The Mean Force Acting on a Small Body in an Axisymmetric Sound Field in a Real Medium", Izvestiva Adademii Nauk SSSR, Mekhanika Zhidkosti I Gaza, 1985, 5, 812-820.
Dean, P.N. et al., "Hydrodynamic Orientation of Sperm Heads for Flow Cytometry", Biophys. J., 1978, 23, 7-13.
Doblhoff-Dier, 0. et al., "A Novel Ultrasonic Resonance Field Device for the Retention of Animal Cells", Biotechnol. Prog., 1994, 10, 428-432.
Doinikov, A.A. et al., "Acoustic radiation force on a spherical particle in a viscous heat-conducting fluid. I. General formula", J. Acoust. Soc. Am., 1997, 101, 713-721.
Doinikov, A.A. et al., "Acoustic radiation force on a spherical particle in a viscous heat-conducting fluid. II. Force on a rigid sphere", J. Acoust. Soc. Am., 1997, 101, 722-730.
Doinikov, A.A. et al., "Acoustic radiation force on a spherical particle in a viscous heat-conducting fluid. III. Force on a liquid drop", J. Acoust. Soc. Am., 1997, 101, 731-740.
Doinikov, A.A. et al., "Acoustic radiation pressure on a rigid sphere in a viscous fluid", Proc. R. Soc. Lond., 1994, 447-466.
Donnert, G. et al., "Major signal increase in fluorescence microscopy through dark-state relaxation", Nature Methods, 2007, 4, 81-86.
Doornbos, R.M. et al., "Experimental and Model Investigations of Bleaching and Saturation of Fluorescence in Flow Cytometry", Cytometry, 1997, 29,204-214.

EPO Application No. EP 08733084: Extended European Search Report dated Mar. 24, 2010.
Fenniri, H. et al., "Classification of Spectroscopically Encoded Resins by Raman Mapping and Infrared Hyperspectral Imaging", Journal of Combinatorial Chemistry, 2006, 8, 192-198.
Fulwyler, M.J. et al., "Hydronamic Orientation of Cells", Histochem. Cytoche., 1977, 7, 781-783.
Gaida, T.H. et al., "Selective Retention of Viable Cells in Ultrasonic Resonance Field Devices", Biotech. Prog., 1996, 12, 73-76.
Gao, X. et al., "Quantum Dot-Encoded Mesoporous Beads with High Brightness and Uniformity: Rapid Readout Using Flow Cytometry", Anal. Chem., 2004, 3, 2406-2410.
Gherardini, L. et al., "A New Immobilisation Method to Arrange Particles in a Gel Matrix by Ultrasound Standing Waves", Ultrasound in Med. & Biol., 1005, 31, 261-272.
Goddard, G. et al., "Single Particle High Resolution Spectral Analysis Flow Cytometry", Cytometry, 2006, 69A, 842-851.
Goddard, G. et al., "Ultrasonic particle concentration in a line-driven cylindrical tube", J. Acoust. Soc. Am., 2005, 117, 3440-3447.
Goddard, G. et al., "Ultrasonic Particle-Concentration for Sheathless Focusing of Particles for Analysis in a Flow Cytometer", Cytometry, 2006, 69, 66-74.
Goddard, G.R. et al., "Ultrasonic Concentration in a Line Driven Cylindrical Tube", Dissertation, 2004, 1-276.
Gonzalez, I. et al., "Precise Measurements of Particle Entertainment in a Standing-Wave Acoustic Field Between 20 and 3500 Hz", J. Aerosol Sci., 2000, 31,1461-1 468.
Gor'Kov, L.P. et al., "On the forces acting on a small particle in an acoustical field in an ideal fluid", Soviet Physics-Doklady, 1962, 6, 773-775.
Gould, R.K. et al., "The effects of acoustic forces on small aprticles in suspension", Proceedings of the 1973 Symposium on Finite Amplitude Wave Effects in Fluids, Bjorno, L., ed., Pergamon, Guildford, 1974, 252-257.
Gould, R.K. et al., "Upper sound pressure limits on particle concentration in fields of ultrasonic standing-wave at megahertz frequencies", Ultrasonics, 1992, 30, 239-244.
Groschl, M. et al., "Automatische Frequenzregelung fur Piezoelektrische Resonatoren und deren Implementierung in akustischen Driftwellenresonator", Diplomarbeit Institut fur Allaemeine Phvsik, Tecnhishchen Universitat Wien, 1991, 1-132.
Grossner, M.T. et al., "Single fiber model of particle retention in an acoustically driven porous mesh", Ultrasonics, 2003, 41, 65-74.
Grossner, M.T. et al., "Single-Collector Experiments and Modeling of Acoustically Aided Mesh Filtration", Amer. Inst. of Chem. Eng., 2005, 51, 1590-1598.
Grossner, M.T. et al., "Transport analysis and model for the performace of an ultrasonically enhanced filtration process", Chem. Ena. Sci., 2005, 60, 3233-3238.
Gupta, S. et al., "Acoustically driven collection of suspended particles within porous media", Ultrasonics, 1997, 35, 131-139.
Gupta, S. et al., "Fractionation of Mixed Particulate Solids According to Compressibility Using Ultrasonic Standing Wave Fields", Chem. Eng. Sci., 1995, 50, 3275-3284.
Haake, A. et al., "Contactless micromanipulation of small particles by an ultrasound field excited by a vibrating body", J. Acoust. Soc. Am., 2005, 117, 2752-2760.
Haake, A. et al., "Manipulation of Cells Using an Ultrasonic Pressure Field", Ultrasound in Med. & Biol., 2005, 31, 857-864.
Haake, A. et al., "Positioning of small particles by an ultrasound field excited by surface waves", Ultrasonics, 2004, 42, 75-80.
Haake, et al., "Positioning, Displacement, and Localization of Cells Using Ultrasonic Forces," Biotechnology and Bioengineering, 92(1), Aug. 10, 2005, pp. 8-14.
Habbersett, R.C. et al., "An Analytical System Based on a Compact Flow Cytometer for DNA Fragment Sizing and Single Molecule Detection", Cytometry 2004, 60A,125-134.
Hager, F. et al., "A Summary of All Forces Acting on Spherical Particles in a Sound Field", Proc. of the Ultrasonic International '91 Conference and Exhibition, Le Touauet, France, 1991, 1-4.
Hamilton, M.F. et al., "Acoustic streaming generated by standing waves in two-dimensional channels of arbitrary width", J. Acoust. Soc. Am., 2003, 113, 153-160.

(56) References Cited

OTHER PUBLICATIONS

Hamilton, M.F. et al., "Linear and nonlinear frequency shifts in acoustical resonators with varying cross sections", J. Acoust. Soc. Am., 2001, 110, 109-119.
Hancock, A., "Observation of Forces on Microparticles in Acoustic Standing Waves", Thesis, submitted in partial satisfaction of the reaquirements for the degree of Master of Science in Biomedical Engineering, University of California, Davis, 2001, 1-155.
Harma, H. et al., "Zeptomole detection sensitivity of prostate-specific antigen in a rapid microtitre plate assay using time-resolved fluorescence", Luminescence, 2000, 15, 351-355.
Harris, N.R. et al., "A silicon microfluidic ultrasonic separator", Sensors and Actuators, 2004, 95, 425-434.
Harrison, B.S. et al., "Near-Infrared Photo- and Electroluminescence of Alkoxy-Substituted Poly (p-phenylene) and Nonconjugated Polymer/Lanthanide Tetraphenylporphyrin Blends", Chemistry of Materials, 2004, 16, 2938-2947.
Hatanaka, S-I et al., "Effect of Process Parameters on Ultrasonic Separation of Dispersed Particles in Liquid", Jpn. J. ADPI. Phys., 1999, 38, 3096-3100.
Hawkes, et al., "Continuous Cell Washing and Mixing Driven by an Unltrsound Standing Wave Within a Microfluidic Channel," Lab Chip, 4, (no month available) 2004, pp. 446-452.
Hawkes, J.J. et al., "A laminar flow expansion chamber facilitating downstream manipulation of particles concentrated using an ultrasonic standing wave", Ultrasonics, 1998, 36, 901-903.
Hawkes, J.J. et al., "Force field particle filter, combinin ultrasound standing waves and laminar flow", Sensors and Actuators B, 2001, 75, 213-222.
Hawkes, J.J. et al., "Microparticle manipulation in millimetre scale ultrasonic standind wave chambers", Ultrasonics, 1998, 36, 925-931.
Hawkes, J.J. et al., "Single half-wavelength ultrasonic particle filter: Predictions of the transfer matrix multilayer resonator model and experimental filtration results", J. Acoust. Soc. Am., 2002, 111, 1259-1266.
Hawkes, J.J. et al., "Ultrasonic deposition of cells on a surface", Biosensors and Bioelectronics, 2004, 19,1021-1028.
Hemmila, I. et al., "Progress in Lanthanides as Luminescent Probes", J. Fluoresncence, 2005, 15, 529-542.
Hertz, H.M. et al., "Standing-wave acoustic trap for nonintrusive positioning of microparticles", J. Appl. Phys., 1995, 78, 4845-4849.
Higashitani, K.O. et al., "Migration of Suspended Particles in Plane Stationary Ultrasonic Field", Chem. Eng. Sci., 1981, 36, 1187-1192.
Hill M. et al., "Modelling in the design of a flow-through ultrasonic separator", Ultrasonics, 2000, 38, 662-665.
Hill M. et al., "Modelling of layered resonators for ultrasonic separation", Ultrasonics, 2002, 40, 385-392.
Hill, D.H. et al., "Operating Characteristics of Acoustically Driven Filtration Processes for Particulate Suspensions", Sep. Sci. and Tech., 2000, 35, 1363-1375.
Hill, M. et al., "The selection of layer thicknesses to control acoustic radiation forces profiles in layered resonators", J. Acoust. Soc. Am., 2003, 114(5), 2654-2661.
Hirschfeld, T. et al., "Fluorescence Background Discrimination by Prebleaching", J. Histochem. and Cytochem., 1979, 27, 96-101.
Holmes, D. et al., "High throughput particle analysis: Combining dielectrophoretic particle focussing with confocal optical detection", Biosensors and Bioelectronics, 2006, 21, 1621-1630.
Holwill, I.L. et al., "The use of ultrasonic standing waves to enhance optical particle sizing equipment", Ultrasonics,2000, 38, 650-653.
Huhtinen, P. et al., "Synthesis, Characterization, and Application of Eu(III), Tb(III), Sm (III), and Dy(III) Lanthanide Chelate Nanoparticle Labels", Anal. Chem., 2005, 77, 2643-2648.
International Application No. PCT/US08/87579: International Search Report dated Feb. 9, 2009.
International Application No. PCT/US2008/059181: International Search Report dated Jul. 25, 2008.
International Application No. PCT/US2009/031154: International Search Report dated Jul. 8, 2009.
Invitrogen, "Fluo-4 NW Calcium Assay Kits (F36205, F36206)", Product Information, 2006.
Invitrogen, "Fluorophore selection guide for flow cytometry", Cellular Analvsis, 2007.
Johnston, P.A. et al., "Cellular platforms for HTS: three case studies", DDT, 2002, 7, 353-363.
Jonsson, H. et al., "Particle separation using ultrasound can be used with human shed mediastinal blodd", Perfusion, 2005, 20, 39-43.
Juarez, J.A. et al., "Piezoelectric Transducer for Air-Borne Ultrasound", Acustica, 1973, 29, 234-239.
Kaduchak, G. et al., "E6 diffraction catastrophe of the primary rainbow of oblate water drops: observations with white-light and laser illumination", Applied Optics, 1994, 33, 4691-4696.
Kaduchak, G. et al., "Hyperbolic umbilic and E6 diffraction catastrophes associated with the secondary rainbow of oblate water drops: observations with laser illumination", Applied Optics, 1994, 33, 4697-4701.
Kapishnikov, S. et al., "Continuous particle size separation and size sorting using ultrasound in a microchannel", J. Stat. Mech., 2006, 1-1 3.
Karumanchi, R.S. et al., "Field-assisted extraction of cells, particles and macromolecules", Trends is Biotech, 2002, 20, 72-78.
Kaye, P.H. et al., "Spatial light-scattering analysis as a means of characterizing and classifying non-spherical particles", Meas. Sci. Technol.,1998, 9, 141-149.
Keij, et al.," Coincidence in High-Speed Flow Cytometry: Models and Measurements," Cytometry 12, Jan. 22, 1991, pp. 398-404.
Kilburn, D.G. et al., "Enhanced Sedimentation of Mammalian Cells following Acoustic Aggregation", Biotech. and Bioeng., 1989, 34, 559-562.
King, L.V. et al., "On the acoustic radiation on spheres", Proc. R. Soc. A., 1933, 147, 212-240.
Kogan, S. et al., "Acoustic concentration of particles in piezoelectric tubes: Theoretical modeling of the effect of cavity shape and symmetry breaking", J. Acoust. Soc. Am., 2004, 116, 1967-1974.
Kozuka, T. et al., "Acoustic Micromanipulation Using a Multi-Electrode Transducer", 7th Inter. Svmp. on Micro Machine and Human Science IEEE, 1996, 163-170.
Kozuka, T. et al., "Control of a Standing Wave Field Using a Line-Focused Transducer for Two-Dimensional Manipulation of Particles", Jpn. J. Appl. Phys., 1998, 37, 2974-2978.
Kozuka, T. et al., "Micromanipulation Using a Focused Ultrasonic Standing Wave Field", Electronics and Communications in Japan, 2000, 83, 1654-1659.
Kumar, M. et al., "Fractionation of Cell Mixtures Using Acoustic and Laminar Flow Fields", Biotech. Bioeng., 2005, 89, 129-137.
Kundt, A. et al., "Longitudinal vibrations and acoustic figures in cylindrical columns of liquids", Annalen der Physik and Chemie (Poggendorff's Annalen), 1874, 153, 1-12.
Kuznetsova, L.A. et al., "Cavitation buble-driven cell and particle behavior in a ultrasound standing wave", J. Acoust. Soc. Am., 2005, 117, 104-112.
Kuznetsova, L.A. et al., "Microparticle concentration in short path length ultrasonic resonators: Roles of radiation pressure and acoustic streaming", J. Acoust. Soc. Am., 2004, 116, 1956-1966.
Kwiatkowski, C.S. et al., "Resonator frequency shift due to ultrasonically induced microparticle migration in an aqueous suspension: Observations and model for the maximum frequency shift", J. Acoust. Soc. Am., 1998, 103, 3290-3300.
Lakowicz, J.R. et al., "On the Possibility of Long-Wavelength Long-Lifetime High-Quantum-Yield Luminophores", Analyical Biochemistry, 2001, 288, 62-75.
Leif, R.C. et al., "Increasing the Luminescence of Lanthanide Complexes", Cytometry, 2006, 69A, 767-778.
Leif, R.C. et al., "Markers for Instrumental Evaluation of Cells of the Female Reproductive Tract; Existing and New Markers", in the Automation of Uterine Cancer Cytology Tutorials of Cytology, (edited by G.L. Wied. et al.), 1976, 313-344.
Lierke, E.G. et al., "Acoustic Positioning for Space Processing of Materials Science Samples in Mirror Furnaces", IEEE Ultrasonics Symposium, 1983, 1129-1139.
Lilliehorn, T. et al., "Trapping of microparticles in the rear field of an ultrasonic transducer", Ultrasonics, 2005, 43, 293-303.

(56) References Cited

OTHER PUBLICATIONS

Lofstedt, R. et al., "Theory of long wavelength acoustic radiation pressure", J. Acoust. Soc. Am., 1991, 90, 2027-2033.
Loken, M.R. et al., "Cell Discrimination by Multiangle Light Scattering", Histochem. Cytochem., 1976, 24, 284-291.
Loken, M.R. et al., "Identification of Cell Asymmetry and Orientation by Light Scattering", Histochem. Cytochem., 1977, 7, 790-795.
Macey, M.G. et al., "Comparative Study of Five Commercial Reagents for Preparing Normal and Leikaemic Lymphoctyes for Immunophenotypic Analysis by Flow Cytometry", Cytometry, 1999, 38,153-160.
Maltsev, V.P. et al., "Scanning flow cytometry for individual particle analysis", Review of Scientific Instruments, 2000, 71, 243-255.
Mandralis, Z. et al., "Enhanced synchronized ultrasonic and flow-field fractionation of suspensions", Ultrasonics, 1994, 32, 113-121.
Mandralis, Z. et al., "Transient Response of Fine Particle Suspensions to Mild Planar Ultrasonic Fields", Fluid/Particle Separation J., 1990, 115-121.
Marston, P.L. et al., "Generalized rainbows and unfolded glories of oblate drops: organization for multiple internal reflection and extension of cusps into Alexander's dark band", Applied Optics, 1994, 33, 4702-4713.
Marston, P.L. et al., "Manipulation of Fluid Objects with Acoustic Radiation Pressure", Ann. N.Y. Acad. Sci., 2004, 1027, 414-434.
Marston, P.L. et al., "Resonances, Radiation Pressure, and Optical Scattering Phenomena of Drops and Bubbles", Proceedings of the Second International Colloquium on Drops and Bubbles, Jet Prop. Lab. Pub 82-7 Pasadena, CA, 1982, 166-174.
Marston, P.L., "Tensile Strength and Visible Ultrasonic Cavitation of Superfluid 4He*," Journal of Low Temperature Physics, 25(3/4), Mar. 5, 1976, pp. 383-407.
Martin, K.M. et al., "Acoustic filtration and sedimentation of soot particles", Experiments in Fluids, 1997, 23, 483-488.
Masudo, T. et al., "Particle Characterization and Separation by a Coupled Acoustic-Gravity Field", Analytical Chemistry 2001, 73, 3467-3471.
Mathies, R.A. et al., "Optimization of High-Sensitivity Fluorescence Detection", Anal. Chem., 1990, 62, 1786-1791.
Mazumdar, M.K. et al., "Single particle aerodynamic relaxation time analyzer", Rev. Sci. Instrum., 1977, 48, 622-624.
Mazumdar, M.K. et al., "Spart Analyzer: Its Application to Aerodynamic Size Distribution Measurement", J. Aerosol Sci., 1979, 10, 561-569.
McCartin, B.J., "A Numerical Procedure for 2D Acoustic Waveguides with Heated Walls", http://flux.aps.org/meetings/YR99/OSS99/abs/S700004.html, 1999.
Meindersma, G.W. et al., "Separation of a biocatalyst with ultrafiltration or filtration after bioconversion", J. Membrane Sci., 1997, 125, 333-349.
Morgan, J. et al., "Manipulation of in vitro toxicant sensors in an ultrasonic standing wave", Toxicology in Vitro, 2004, 18, 115-120.
Mullaney, P.F, et al., "The Small Angle Light Scattering of Biological Cells", Biophys. J., 1970, 10, 764-772.
Neild, A. et al., "Design, modeling and characterization of microfluidic devices for ultrasonic manipulation", Sensors and Actuators B: Chemical , Feb. 20, 2007, 121(2).
Neild, A., "A micro-particle positioning technique combining an ultrasound manipulator and a microgripper," J. Micromechanical Microengineering, 2006, 16, 1562-1570.
Neukammer, J. et al., "Angular distribution of light scattered by single biological cells and oriented particle agglomerates", Appl. Opt., 2003, 42, 6388-6397.
Nilsson, A. et al., "Acoustic control of suspended particles in micro fluidic chips", Lab Chip, 2004, 4, 131-135.
Nolan et al., "Suspension Array Technology: New Tools fro Gene and Protein Analysis", Cell and Molecular Biology, 2001, 47, 1241-1256.
Nowotny, H. et al., "Layered piezoelectric resonators with an arbitrary number electrodes (general one-dimensional treatment)", J. Acoust. Soc. Am., 1991, 90, 1238-1245.
Otaki, M. et al., "Virus Removal in a Membrane Separation Process", Water Sci. and Tech., 1998 37, 107-116.
Pangu, G.D. et al., "Acoustically aided separation of oil droplets from aqueous emulsions", Chem. Eng. Sci., 2004, 59, 3183-3193.
Petersson, F. et al., "Carrier Medium Exchange through Ultrasonic Particle Switching in Microfluidic Channels", Anal. Chem., 2005, 77, 1216-1221.
Petersson, F. et al., "Continuous separation of lipid particles from erythrocytes by means of laminar flow and acoustic standing wave forces", Lab Chip, 2005, 5, 20-22.
Petersson, F. et al., "Free Flow Acoustophoresis: Microfluidic-Based Mode of Particle and Cell Separation", Anal. Chem., 2007 79, 5117-5123.
Petersson, F., "Particle Flow Switch Utilizing Ultrasonic Particle Switching in Microfluidic Channels", 7th International Conf on Miniaturizing Chem and Biochem Analysis Systems, 2003, 879-882.
Pregibon, D.C. et al., "Multifunctional Encoded Particles for High-Throughput Biomolecule Analysis", Science, 2007, 315, 1393-1396.
Princen, K. et al., "Evaluation of SDF-1/CXCR4-Induced Ca2+Signaling by Fluorometric Imaging Plate Reader (FLIPR) and Flow Cytometry", Cytometry, 2003, 51A, 35-45.
Pui, P.W. et al., "Batch and Semicontinuous Aggregattion and Sedimentation of Hybridoma Cells by Acoustic Resonance Fields", Biotechnol. Prog., 1995, 11, 146-152.
Rama Rao, G.V. et al., "Monodisperse Mesoporous Silica Microspheres Formed by Evaporation-Induced Self Assembly of Surfacant Templates in Aerosols", Advanced Materials, 2002, 18,1301-1304.
Rens, W. et al., "A Novel Nouel for More Efficient Sperm Orientation to Improve Sorting Efficiency of X and Y Chromosome-Bearing Sperm", Cytometry, 1998, 33, 476-481.
Ricks, D.C. et al., "A numerically stable global matrix method for cylindrically layered shells excited by ring forces", J. Acoust. Soc. Am., 1994, 95, 3339-3349.
Rouleau, F. et al., "Electromagnetic scattering by compact clusters of spheres", Astron. Astrophys., 1996, 310, 686-698.
Rudnick, J. et al., "Oscillational instabilities in single-mode acoustic levitators", J. Acoust. Soc. Am., 1990, 87, 81-92.
Saito, M. et al., "Microorganism manipulation and microparticle arrangement by the use of ultrasonic standing waves", SPIE, 2001, 4590, 26-37.
Saito, M. et al., "Quantum mechanical representation of acoustic streaming and acoustic radiation pressure", Physical Review, 2001, E64, 026311-1-026311-5.
Saito, M. et al., "Ultrasonic manipulation of locomotive microorganisms and evaluation of their activity", J. App. Physics, 2002, 92, 7581-7586.
Saito, M. et al., "Ultrasonic trapping of paramecia and estimation of their locomotive force", Appl. Phys. Lett,1997, 71,1909-1911.
Saito, M. et al., "Ultrasonic waves for fabricating lattice structure in composite materials", SPIE, 1999, 3786, 179-190.
Samiotaki, M. et al., "Seven-Color Time-Resolved Fluorescence Hybridization Analysis of Human Papilloma Virus Types", Analytical Biochem., 1997, 253, 156-161.
Schmid, M. et al., "A computer-controlled system for the measurement of complete admittance spectra of piezoelectric resonators", Meas. Sci. Technol., 1990, 1, 970-975.
Schoell, W.M. et al., "Separation of Sperm and Vaginal Cells with Flow Cytometry for DNA Typing After Sexual Assault", Obstetrics and Gynecolony, 1999, 94, 623-627.
Semianov, K.A. et al., "Measurement of Mammalian Erythrocyte Indices from Light Scattering with Scaning Flow Cytometer", Proc. SPIE, 2003, 5141,106-113.
Sethu, P. et al., "Continuous Flow Microfluidic Device for Rapid Erythrocyte Lysis", Anal. Chem., 2004, 76, 6247-6253.
Shapiro, H.M. et al., Practical Flow Cytometry, Hoboken, NJ, John Wiley & Sons. Inc., 2005, 9-13.

(56) References Cited

OTHER PUBLICATIONS

Shvalov, A.N. et al., "Individual *Escherichia coli* Cells Studied from Light Scattering with the Scanning Flow Cytometer", Cytometry, 2000, 41, 41-45.
Shvalov, A.N. et al., "Light-scattering properties of individual erythrocytes", Applied Optics, 1999, 38, 230-235.
Simpson, H.J. et al., "Ultrasonic four-wave mixing mediated by an aqueous suspension of microspheres: Theoretical steady-state properties", J. Acoust. Soc. Am., 1995, 98, 1731-1741.
Skudrzyk, E. et al., "Die Grundlagen der Akustic", Sprinaer Verlaa. Wien, 1954, 202-205 and 807-825.
Slomkowski, S. et al., "New Types of Microspheres and Microsphere-related Materials for Medical Diagnostics", Polymers for Advanced Technologies, 2002, 13, 906-918.
Sobanski, M.A. et al., "Sub-micron particle manipulation in an ultrasonic standing wave: Applications in detection of clinically important biomolecules", Bioseparation, 2001, 9, 351-357.
Steinkamp, J.A. et al., "Dual-Laser, Differential Fluorescence Correction Method for Reducing Cellular Background Autofluorescence", Cytometry,1986, 7, 566-574.
Steinkamp, J.A. et al., "Enhanced Immunofluorescence Measurement Resolution of Surface Antigens on Highly Autofluorescent, Glutaraldehyde-Fixed Cells Analyzed by Phase-Sensitive Flow Cytometry", Cytometry, 1999, 37, 275-283.
Steinkamp, J.A., "A Differential Amplifier Circuit for Reducing Noise in Axial Light Loss Measurements", Cyometry, 1983, 4, 83-87.
Stewart, C.C. et al., "Resolving Leukocytes Using Axial Light Loss", Cytometry, 1989, 10, 426-432.
Stoffel, C.L. et al., "Data Analysis for a Dual Analysis for a Dual-Channel Virus Counter", Analytical Chemistry, 2005, 77, 2243-2246.
Stoffel, C.L. et al., "Design and Characterization of a Compact Dual Channel Virus Counter", Cytometry, 2005, Part A 65A, 140-147.
Stovel, R.T. et al., "A Means for Orienting Flat Cells in Flow Systems", Biophys J., 1978, 23, 1-5.
Takeuchi, J. et al., "Ultrasonic Micromanipulator Using Visual Feedback", Jpn J. Appl. Phys., 1996, 35, 3244-3247.
Takeuchi, M. et al., "Ultrasonic Micromanipulation of Small Particles in Liquid", Jpn J. Appl. Phys., 1994, 33, 3045-3047.
Thiessen, D.B. et al., "Principles of some Acoustical, Electrical, and Optical Manipulation Methods with Applications to Drops, Bubbles, and Capillary Bridges", ASME Fluids Eng. Div. Publ. FED, 1998.
Thiessen, D.B. et al., "Some Responses of Small Diffusion Flames to Ultrasonic Radiation", NASA, 2003, 321-324.
Tolt, T.L. et al., "Separation devices based on forced coincidence response of fluid-filled pipes", J. Acoust. Soc. Am., 1992, 91, 3152-3156.
Tolt, T.L. et al., "Separation of Dispersed Phases from Liquids in Acoustically Driven Chambers", Chem. Eng. Science, 1993, 48, 527-540.
Townsend, R.J. et al., "Modelling of particle paths passing through an ultrasonic standing wave", Ultrasonics, 2004, 42, 319-324.
Trihn, E.H. et al., "Experimental study of streaming flows associated with ultrasonic levitators", Phys. Fluids, 1994, 6, 3567-3579.
Trinh, E.H. et al., "Compact acoustic levitation device for studies in fluid dynamics and material science in the laboratory and microgravity", Rev. Sci. Instrum., 1985, 56, 2059-2065.
Tuckermann, R. et al., "Trapping of heavy gases in stationary ultrasonic fields", Chem. Phys. Ltrs., 2002, 363, 349-354.
Tung, Yi-C. et al., "PDMS-based opto-fluidic micro flow cytometer with two-color, multi-angle fluorescence detection capability using PIN photodiodes", Sensors and Actuators, 2004, 98, 356-367.
Tyson, D.S. et al., "Ruthenium (II) complex with a notably long excited state lifetime", The Royal Society of Chemistry, 2000, 2355-2356.
United States Patent and Trademark Office: Final Office Action dated Dec. 31, 2008, U.S. Appl. No. 11/784,936.

United States Patent and Trademark Office: Final Rejection dated Jul. 7, 2010, U.S. Appl. No. 11/784,928.
United States Patent and Trademark Office: Non-Final Office Action dated Jun. 10, 2010, U.S. Appl. No. 11/982,042.
United States Patent and Trademark Office: Non-Final Office Action dated Dec. 30, 2009, U.S. Appl. No. 11/784,928.
United States Patent and Trademark Office: Non-Final Office Action dated Apr. 3, 2008, U.S. Appl. No. 11/784,936.
United States Patent and Trademark Office: Non-Final Office Action dated Jun. 24, 2009, U.S. Appl. No. 11/784,936.
United States Patent and Trademark Office: Notice of Allowance dated Feb. 22, 2010, U.S. Appl. No. 11/784,936.
United States Patent and Trademark Office: Restriction Requirement dated Nov. 30, 2009, U.S. Appl. No. 11/982,042.
United States Patent and Trademark Office: Restriction Requirement dated Jul. 1, 2009, U.S. Appl. No. 11/784,928.
Vainshtein, P. et al., "On the Drift of Aerosol Particles in Sonic Fields", J. Aerosol Sci., 1992, 23, 631-637.
Vainshtein, P. et al., "The effect of centreline particle concentration in a wave tube", J. Fluid Mech., 1996, 306, 31-42.
Van Hee, P. et al., "Strategy for Selection of Methods for Separation of Bioparticles From Particle Mixtures", Biotech. Bioeng., 2006, 94, 689-709.
Verpoorte, E. et al., "Beads and chips: new recipes for analysis— Elisabeth Verpoorte reviews particle handling in microchannels", Lab Chip, 2003, 3, 60N-68N.
Visuri, S.V. et al., "Microfluidic tolls for biological sample preparation", Poster 1423, 2nd Annual International IEEE-EMBS Special Topic Cofnerence on Microtechnologies in Medicine & Biology, May 2-24, 2002 556-559.
Wang, Z. et al., "Retention and Viability Characteristics of Mammalian Cells in an Acoustically Driven Polymer Mesh", Biotechnol. Prog., 2004, 20, 384-387.
Ward, M. et al., "Manipulation of Immunomagnetic Targets in Microfluidic Channel Flow", Dissertation, 2005, 1-205.
Weiser, M.A. et al., "Interparticle Forces on Red Cells in a Standing Wave Field", Acustica, 1984, 56, 114-119.
Weiser, M.A.H. et al., "Extension of acoustic levitation to include the study of micron-size particles in a more compressible host liquid", J. Acoust. Soc. Am., 1982, 71, 1261-1268.
Whitworth, G. et al., "Particle column formation in a stationary ultrasonic field", J. Acoust. Soc. Am., 1992, 91, 79-85.
Whitworth, G. et al., "Transport and harvesting of suspended particles using modulated ultrasound", Ultrasonics, 1991, 29, 439-444.
Wu, Y. et al., "Diazo Coupling Method for Covalent Attachment of Proteins to Solid Substrates", Bioconjugate Chem., 2006, 17, 359-365.
Yagi, et al., "Flow Cytometry to Evaluate Theileria Sergenti Parasitemia Using the Florescent Nucleic Acid Stain SYTO16," Cytometry, 41, (no month available) 2000, pp. 223-225.
Yamakoshi, Y. et al., "Micro particle trapping by opposite phases ultrasonic travelling waves", Ultrasonics, 1998, 36, 873-878.
Yasuda, K. et al., "Blood Concentration by Superposition of Higher Harmonics of Ultrasound", Jpn. J. Appl. Phys., 1997, 36, 3130-3135.
Yasuda, K. et al., "Concentration and Fractionation of Small Particles in Liquid by Ultrasound", Jpn J. Appl. Phys., 1995, 34, 2715-2720.
Yasuda, K. et al., "Deoxyribonucleic acid concentration using acoustic radiation force", J. Acoust. Soc. Am., 1996, 99, 1248-1251.
Yasuda, K. et al., "Non-destructive, non-contact handling method for biomaterials in micro-chamber by ultrasound", Sensors and Actuators, 2000, 64, 128-135.
Yasuda, K. et al., "Particle separation using acoustic radiation force and elecrostatic force", J. Acoust. Soc. Am., 1996, 99, 1965-1970.
Yasuda, K. et al., "Using acousitc radiation force as a concentration method for erythrocytes", J. Acoust. Soc. Am., 1997, 102, 642-645.
Ye, C-H. et at., "Preparation of three terbium complexes with paminobenzoic acid and investigation of crystal structure influence on luminescence property", Journal of Solid State Chemistry, 2004, 177, 3735-3742.

(56) References Cited

OTHER PUBLICATIONS

Yosioka, K. et al., "Acoustic Radiation Pressure on a Comressible Sphere", Acustica, 1955, 5, 167-173.
Yuan, J. et al., "Lanthanide-based luminescence probes and time-resolved luminescence bioassays", Trends in Analytical Chemistry, 2006, 25, 490-500.
Yurkin, M.A. et al., "Experimental and theoretical study of light scattering by individual mature red blook cells by use of scanning flow cytometry and a discrete dipole approximation", Applied Optics, 2005, 44, 5249-5256.
U.S. Appl. No. 11/982,042: Final Office Action dated Oct. 17, 2011.
U.S. Appl. No. 12/283,491: Non-Final Office Action dated Sep. 27, 2011.
U.S. Appl. No. 12/283,461: Non-Final Office Action dated Sep. 26, 2011.
U.S. Appl. No. 12/903,003: Non-Final Office Action dated Oct. 24, 2011.
U.S. Appl. No. 12/903,003: Final Office Action dated Feb. 6, 2012.
U.S. Appl. No. 12/283,491: Ex parte Quayle Action dated Mar. 29, 2012.
U.S. Appl. No. 12/283,491: Notice of Allowance dated May 25, 2012.
U.S. Appl. No. 12/283,461: Ex parte Quayle Action dated Mar. 29, 2012.
U.S. Appl. No. 12/283,461: Notice of Allowance dated May 31, 2012.
U.S. Appl. No. 12/903,003: Non-Final Office Action dated Jun. 19, 2012.
U.S. Appl. No. 13/295,934: Non-Final Office Action dated Oct. 9, 2012.
U.S. Appl. No. 12/903,003: Final Office Action dated Oct. 24, 2012.
U.S. Appl. No. 12/903,003: Non-Final Office Action dated Feb. 13, 2013.
Anderson, M.J. et al., "Use of Acoustic Radiation Pressure to Concentrate Small Particles in an Air Flow," 2002 IEEE Ultrasonics Symposium, Jan. 1, 2002, 481-484.
U.S. Appl. No. 12/903,003: Notice of Allowance dated Jun. 5, 2013.
U.S. Appl. No. 13/295,934: Non-Final Office Action dated May 24, 2013.
U.S. Appl. No. 13/571,629: Restriction Requirement dated Dec. 6, 2013, 10 pages.
U.S. Appl. No. 13/618,237: Non-Final Office Action dated Jan. 27, 2014, 13 pages.
U.S. Appl. No. 13/966,624: Final Office Action dated Jan. 28, 2014, 15 pages.
U.S. Appl. No. 11/982,042: Non-Final Office Action dated Oct. 22, 2013.
U.S. Appl. No. 13/966,624: Non-Final Office Action dated Sep. 24, 2013.
U.S. Appl. No. 13/618,237: Restriction Requirement dated Sep. 3, 2013.

\* cited by examiner

ACOUSTIC CONCENTRATION OF PARTICLES IN FLUID FLOW

CROSS-REFERENCE TO RELATED APPLICATIONS

This application is a continuation of U.S. patent application Ser. No. 11/784,936, filed on Apr. 9, 2007, the contents of which is incorporated by reference herein in its entirety.

STATEMENT REGARDING FEDERALLY SPONSORED RESEARCH OR DEVELOPMENT

This invention was made with Government support under Contract Number DE-AC51-06NA25396 awarded by the United States Department of Energy. The Government has certain rights in the invention.

BACKGROUND

The present invention relates in general to field-based separation of particles in a medium utilizing acoustic pressure.

Field-based separation of particles in fluid has been explored for numerous applications from high gradient magnetic separation of nuclear fuel waste particles to dielectrophoretic separation of live and dead bacteria to acoustic separation of blood cells from serum.

The ability to push cells or particles to the top of a channel enables concentration of particulate matter in fluids by forcing them to slower streamlines in a laminar flow regime or by trapping them altogether if the viscous drag is less than the trapping force. Particles and/or cells so trapped can also be held and washed or exposed to other fluids and/or reagents.

It is desirable to provide a device for acoustic concentration and trapping of particles within a medium using acoustic radiation pressure.

SUMMARY

An apparatus and method for acoustic concentration of particles in a fluid flow includes a substantially acoustically transparent membrane and a vibration generator that define a fluid flow path therebetween. The fluid flow path is in fluid communication with a fluid source and a fluid outlet and the vibration generator is disposed adjacent the fluid flow path and is capable of producing an acoustic field in the fluid flow path. The acoustic field produces at least one pressure minima in the fluid flow path at a predetermined location within the fluid flow path and forces predetermined particles in the fluid flow path to the at least one pressure minima.

In one embodiment, the membrane may be formed from Mylar, glass mica, polymers, or combinations thereof. The predetermined location in the fluid flow path may be adjacent a membrane wall. The predetermined dimension may be a function of the resonance of the fluid source. The predetermined location may be a function of a wavelength of the acoustic field produced by the vibration generator and may be ¼ of the wavelength of the acoustic field or ⅝ of the wavelength of the acoustic field. The vibration generator may be a piezoelectric transducer. The predetermined particles may be positive acoustic contrast particles.

Alternatively, the membrane is permeable. Reagents may diffuse through the membrane to the predetermined particles in the flow path when flow is stopped in the flow path. Alternatively, the apparatus further comprises a matching layer intermediate the vibration generator and the flow path. The matching layer may be a ¼ wavelength matching layer. Alternatively, the wall of the membrane accommodates high power microscopic observation of the particles in the flow path. The predetermined particles may be particles selected from the group consisting of particles of different sizes and particles with different acoustic contrasts and the apparatus may perform field flow fractionation.

The present invention comprises an apparatus and method used to separate, concentrate, trap or focus particles in fluid using ultrasonic standing waves. The apparatuses are preferably constructed using a vibration generator such as a piezoelectric transducer to drive resonant modes in a channel or chamber with a membrane top such that particles with positive acoustic contrast are driven to the membrane or to other points of minimum pressure in the standing wave generated by the vibration generator.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF ILLUSTRATIVE EMBODIMENTS

Successful meso- to microfluidic sample preparation is dependent upon efficient sorting, concentration, and washing of targets. Numerous successful analytical lab-on-a-chip micro-devices capable of a wide range of detection techniques from spectroscopy to gene detection have been demonstrated in both clinical and homeland security arenas. In the present evolution of these devices, however, their increased application to real world problems of interest has been severely limited by inadequate provisions for handling samples. The heart of this problem lies in concentrating and purifying a large dilute sample that contains interferents. These microfabricated devices generally require a clean sample with a representative population of target species that can be analyzed only in microliter and nanoliter volumes. In applications where the sample volume is measured in milliliters to liters, the sample preparation is a daunting task that has not been adequately addressed.

Several field-based methods for sample processing have been applied to this problem including immunomagnetic separation, electrophoresis, dielectrophoresis and ultrasonic separation. Ultrasonic separation is particularly attractive for many applications as it typically does not require reagents and can be performed in complex media with little regard for sample conductivity or pH.

Ultrasonic separation is typically achieved in resonant chambers in which standing waves are established using a vibration generator, such as a piezoelectric transducer or the like. The force on a particle is given by the following equation derived by Gor'kov:

$$F = -\nabla \left( \frac{2}{3} \pi R^3 \left[ \frac{Z_0}{\rho_f c_f^2} \overline{p^2} - \frac{3Z_1 \rho_f}{2} \overline{v^2} \right] \right)$$

Where R is particle radius, $\rho_f$ is fluid density $c_f$ is fluid sound speed $p^2$ is mean square fluctuations of pressure at the particle, $v^2$ is mean square fluctuations of velocity at the particle and $Z_0$ and $Z_1$ are functions of particle and fluid properties called acoustic contrast factors. Most particles and cells of interest have positive acoustic contrast in water or buffers and therefore they typically migrate to positions of lowest pressure (pressure nodes or pressure minima). Materials such as fat globules and gas bubbles have negative acoustic contrast and tend to move toward positions of highest pressure (pressure antinodes or pressure maxima).

Figure 1:
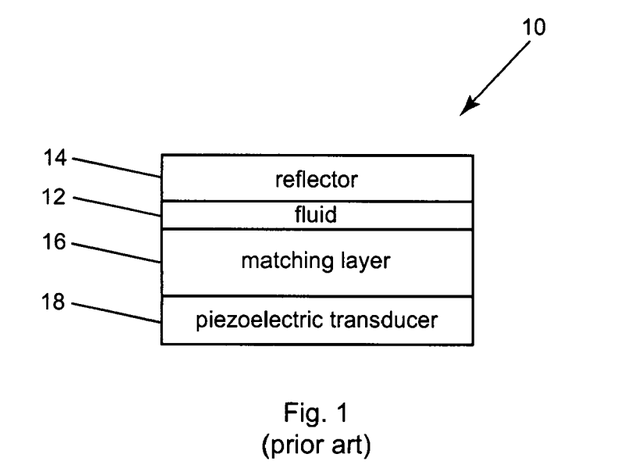
FIG. 1 is a schematic view of a separator according to the prior art.

Referring to FIG. 1, an ultrasonic separator in accordance with the prior art is indicated generally at 10. Separator 10 includes fluid channel 12, ½ wavelength glass acoustic reflector top 14 and ¾ wavelength matching layer resonator bottom 16 coupled to transducer 18. Typically, separator 10 operates at a resonant frequency approximately ½ or ¼ wavelength of fluid layer 12. The thickness and composition of the material of top reflector 14 and bottom matching layer 16 are chosen such that the phase relationship of incident and reflected waves results in a pressure node or pressure minima either at the center of fluid channel 12 or at the surface of the top reflector 14. Separator 10 uses acoustic standing waves in channel 12 to force particles with positive acoustic contrast to move towards one wall of the channel. Device 10 is tuned such that a standing wave can be established for which a pressure node or minima forces particles with positive acoustic contrast to migrate toward top of channel 12.

Figure 2:
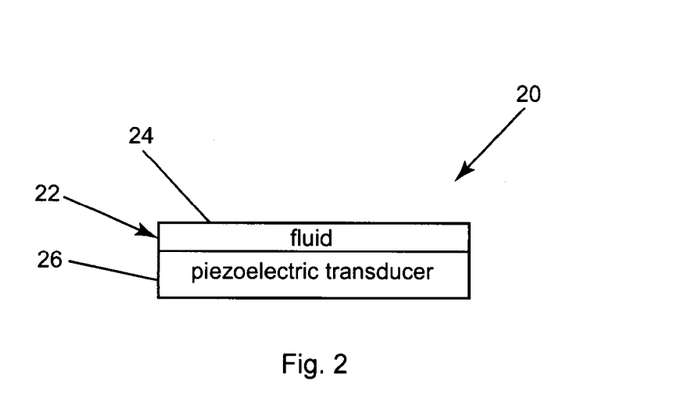
FIG. 2 is a schematic view of an embodiment of an apparatus in accordance with the present invention.

Referring to FIG. 2, an embodiment of apparatus in accordance with the present invention is indicated generally at 20. Apparatus 20 includes fluid flow path or channel 22 preferably in fluid communication with a fluid source (not shown) and a fluid outlet (not shown) having membrane 24 as a top surface coupled to vibration generator 26 disposed adjacent flow channel 22. Flow channel 22 is preferably defined by an upper surface of vibration generator 26 and by membrane 24. The fluid source may supply water, or any suitable liquid to flow path or channel 22, as will be appreciated by those skilled in the art. Fluid flow path or channel 22 preferably has a predetermined dimension that is a function of the resonance of the fluid source. Preferably, vibration generator 26 is a piezoelectric transducer. Alternatively, vibration generator 26 is a line-drive element, a displacement generator, or any other type of vibration generator capable of producing an acoustic or displacement field within fluid channel 22. When vibration generator 26 is driven, plane waves incident on the boundary of membrane 24 are reflected back out of phase. Membrane 24 functions as a pressure release surface with a reflection coefficient of near −1. Therefore, the reflected wave is 180 degrees out of phase with the incident wave and the pressure wave is 90 degrees out of phase with the displacement wave. This results in a pressure node or minima at the surface of membrane 24, best seen in FIG. 3 and discussed in more detail below. Membrane 24 can be made of any suitable material but it should be thin enough to be substantially acoustically transparent to the acoustic wave generated by vibration generator 26 such as, but not limited to, thin Mylar, glass, mica or similar suitable materials.

Figure 3:
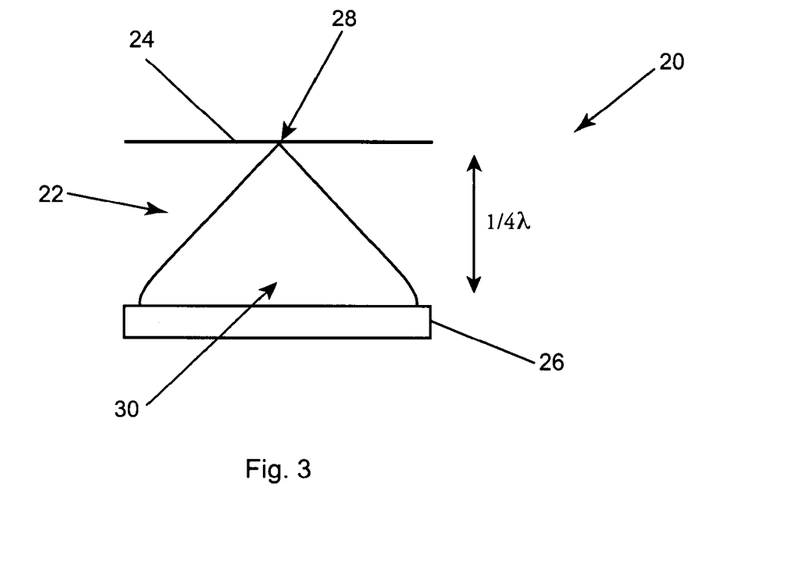
FIG. 3 is a schematic graph showing the location of pressure nodes and antinodes in the apparatus of FIG. 2.
Figure 6:
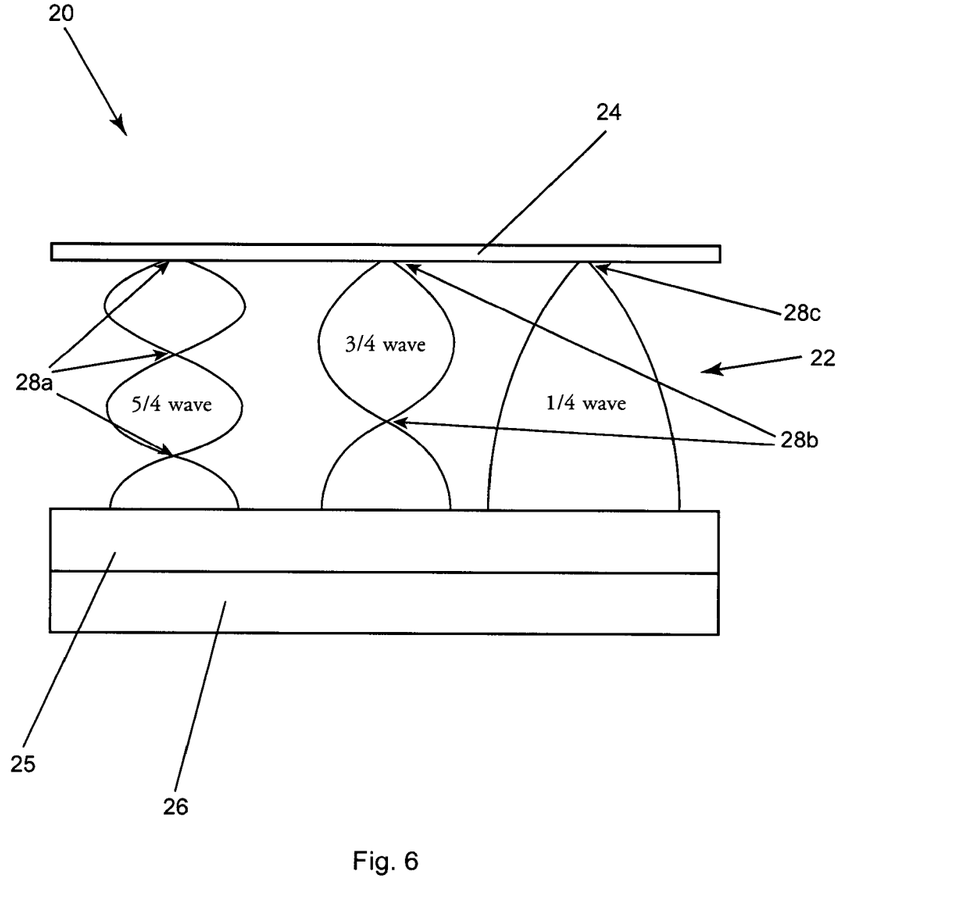
FIG. 6 is a schematic view of an embodiment of an apparatus in accordance with the present invention showing profiles of various pressure minima.

There is shown in FIG. 3 a pressure profile in fluid flow path or channel 22 indicating pressure node or minima 28 adjacent membrane 24 and pressure antinode or maxima 30 adjacent vibration generator 26. The thickness of channel 22 thickness is ¼ wavelength (λ) of the resonance. Particles and/or cells with positive acoustic contrast are driven to the surface of membrane 24 surface or pressure node 28. Pressure nodes 28 can also be created within the fluid by tuning fluid layer 22 to alternate frequencies e.g. ¾ or ⅝ λ. For example, there is shown in FIG. 6, various locations of pressure minima 28a, 28b, and 28c in flow path or channel 22 of apparatus 20, based on the resonance of medium disposed in the fluid layer in flow channel 22. Pressure minima 28a for a ⅝ wavelength is shown in three locations within channel 22. Pressure minima 28b for a ¾ wavelength is shown at a pair of locations within channel 22 and pressure minima 28c for a ¼ wavelength is shown at a single location adjacent membrane 24. Those skilled in the art will appreciate that pressure minima, such as pressure minima 28a, 28b, and 28c may be located at any predetermined location within channel 22 between vibration generator 26 and membrane 24 and that the predetermined location is a function of the resonance and frequency of the fluid source and the predetermined dimension of flow channel 22 between vibration generator 26 and membrane 24. Alternatively, apparatus 20 includes a ¼ wavelength matching layer 25 on an upper surface of vibration generator 26 opposite membrane 24. Matching layer 25 is preferably a ¼ wavelength matching layer and is operable to isolate vibration generator 26 from the fluid within channel 22 and/or to better match the acoustic impedance of the fluid within channel 22.

Figure 4:
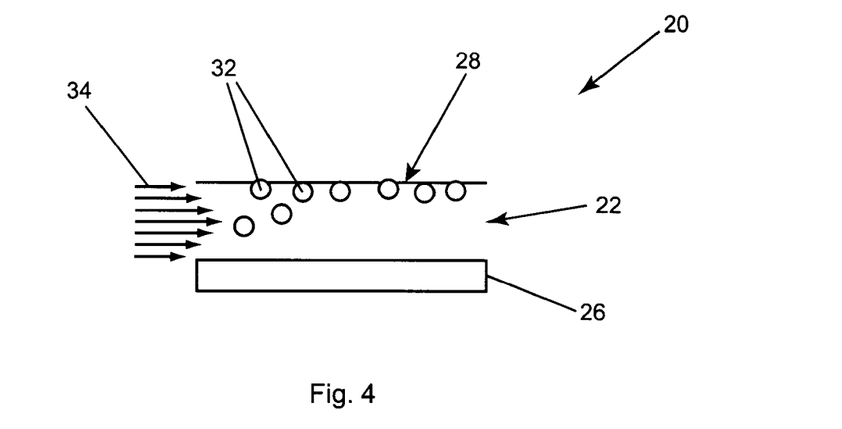
FIG. 4 is a schematic view of particles being separated by the apparatus of FIG. 2.

Apparatus 20 can be applied to separate and or concentrate target particles and cells. When device 20 is embodied as a channel 22 with laminar flow, indicated by arrow 34, particles or cells 32 are forced into slower streamlines where they become concentrated, best seen in FIG. 4. For particles 32 of different sizes or with different acoustic contrasts, device 20 can perform field flow fractionation (FFF), as will be appreciated by those skilled in the art. In FIG. 4, particles or cells 32 with larger volumes or greater acoustic contrast are forced to surface of membrane 24 more quickly.

Alternatively, when the flow of the fluid in device 20 is slowed sufficiently or stopped altogether, particles or cells 32 are trapped at surface of membrane 24. There, particles or cells 32 are washed or exposed to other reagents. This is preferably done by replacing the sample fluid in channel 22 or, if membrane 24 is made permeable, reagents are preferably added to the opposite side of membrane 24 where the reagents can diffuse through membrane 24 to the trapped targets 32.

Figure 5A:
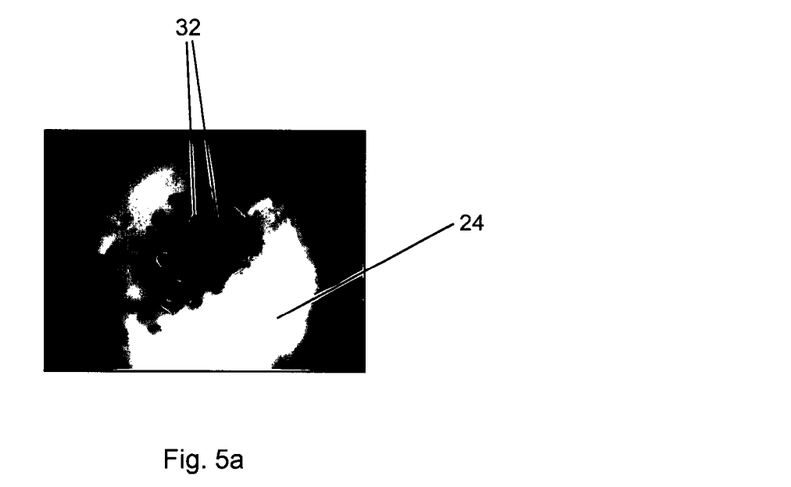
FIGS. 5a and 5b are microscopic photographs showing latex particles acoustically trapped on a membrane surface of the apparatus.
Figure 5B:
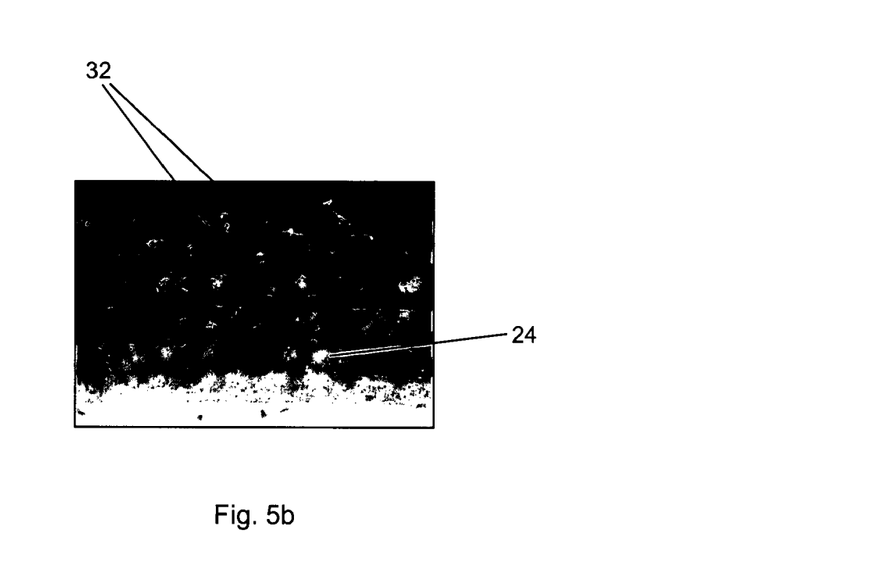

Thin membrane 24 advantageously allows optical observation with high numerical aperture close working distance lenses (not shown). This is useful in applications in oncology or microbiology. In addition, cells or particles 32 can be observed in an imaging plane in flow away from the membrane if an alternate tuning that provides for pressure nodes or minima in the fluid is used. In FIGS. 5a and 5b there is shown microscopic photographs of test results for apparatus 20 using 3 micron red latex particles 32. Particles 32 are trapped on the surface of membrane 24.

For apparatus 20, it is only necessary to tune to the resonance of the fluid layer (¼, ¾, 5/4, etc wavelength). It is therefore simpler to accommodate fluid property or temperature changes that may affect the tuning of apparatus 20. Added advantages to the membrane configuration of apparatus 20 include possible viewing of trapped or moving plane focused species with close working distance objectives and possible incorporation of particular membrane properties, such as selective permeability.

Acoustic separations utilizing apparatus 20 can advantageously be accomplished without the use of reagents and without regard for fluid pH or conductivity, making apparatus 20 well suited for use in complex media such as blood or sewer water. Apparatus 20 uses membrane top 24 that can be fabricated inexpensively from polymers. Membrane top 24 is thin enough to accommodate high power microscopic observation of trapped species 32. Membrane 24 can also advantageously be made selectively permeable such that reagents or analytes could diffuse across membrane 24.

The primary commercial applications for apparatus 20 are contemplated to be sample preparation (concentration/separation/washing) and imaging for medical, industrial, and environmental samples. Apparatus 20 of the present invention pushes positive acoustic contrast particles 32 to channel wall 24 opposite vibration generator 26 that comprises a thin membrane top 24, which advantageously eliminates the need for precise tuning of paired matching layer 16 and reflector 14 as in the prior art device 10 shown in FIG. 1.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above and/or in the attachments, and of the corresponding application(s), are hereby incorporated by reference.

What is claimed:

1. A system for observing one or more particles in a fluid, the system comprising:
   a flow chamber,
   a portion of the flow chamber comprising a selectively transmissive membrane having a first side and a second side;
   a vibration generator disposed on the flow chamber;
   a flow path for the fluid being defined directly between a surface of the vibration generator and the first side of the selectively transmissive membrane, such that the second side of the selectively transmissive membrane remains free from contact with the fluid during operation; and
   a microscope configured to observe the one or more particles flowing in the flow path;
   the vibration generator being configured to produce an acoustic field in the flow path that forces particles in the flow path to the at least one pressure minima.

2. The system of claim 1 wherein the microscope is configured to observe the one or more particles through the selectively transmissive membrane.

3. The system of claim 1 wherein the vibration generator is a line drive element.

4. The system of claim 1 wherein the vibration generator is configured to field flow fractionate the one or more particles in the flow chamber.

5. The system of claim 1 wherein the selectively transmissive membrane is transparent.

6. The system of claim 2 wherein the microscope is configured to observe the one or more particles through the selectively transmissive membrane when one or more particles are adjacent to the selectively transmissive membrane.

7. The system of claim 2 wherein the microscope is configured to observe the one or more particles through the selectively transmissive membrane when the one or more particles are in a pressure node positioned within the flow path.

8. A system for manipulating one or more particles in a fluid, the system comprising:
   a flow chamber defining a flow path for a fluid, the fluid including one or more particles;
   a membrane having a first side and a second side, the membrane arranged on a portion of the flow chamber, the membrane being configured to selectively allow one or more substances into the fluid flow path; and
   a vibration generator disposed on said flow chamber,
   the flow path being defined directly between a the first side of the membrane and a surface of the vibration generator such that the second side of the membrane remains free from contact with the fluid during operation.

9. The system of claim 8 wherein the flow chamber is configured to stop the flow of the fluid.

10. The system of claim 8 wherein the vibration generator is a line drive element.

11. The system of claim 8 wherein the vibration generator is configured to field flow fractionate the particles.

12. The system of claim 9 wherein the flow chamber is configured to stop the one or more particles adjacent to the membrane.

13. The system of claim 9 wherein the membrane is configured to selectively allow the one or more substances to interact with the one or more particles.

14. A method for selectively exposing one or more particles in a fluid to one or more substances, the method comprising:
   flowing one or more particles at a first speed in a flow path within a flow chamber, a portion of the flow chamber comprising a selectively transmissive membrane having a first side and a second side;
   applying acoustic radiation perpendicular to the flow path from a source of acoustic radiation to the one or more particles while the particles are disposed in a flow path directly between and only between the first side of the selectively transmissive membrane and a surface of the source of acoustic radiation such that the second side of the selectively transmissive membrane remains free from contact with the fluid during operation; and
   exposing, via the selectively transmissive membrane, the one or more particles to one or more substances.

15. The method of claim 14 further comprising observing, through said membrane, the one or more particles flowing at the second speed with a microscope.

16. The method of claim 14 wherein the acoustic radiation is applied by a line drive element.

17. The method of claim 14 further comprising performing field flow fractionation on the one or more particles.

18. The method of claim 15 wherein the second speed is stopped.

19. The method of claim 18 further comprising stopping the one or more particles adjacent to the membrane.

20. The method of claim 18 further comprising stopping the one or more particles in a pressure node positioned within the flow chamber.

* * * * *

UNITED STATES PATENT AND TRADEMARK OFFICE
CERTIFICATE OF CORRECTION

PATENT NO.      : 9,733,171 B2
APPLICATION NO. : 12/903042
DATED           : August 15, 2017
INVENTOR(S)     : Michael D. Ward and Gregory Kaduchak It is certified that error appears in the above-identified patent and that said Letters Patent is hereby corrected as shown below:

On the Title Page

Item (75), Inventors:
Line 1, delete "Michael W. Ward," and insert -- Michael D. Ward, --.

Item (57), ABSTRACT:
Line 1, delete "a acoustic" and insert -- acoustic --.

Item (56), References Cited "OTHER PUBLICATIONS:

Page 3, Column 2:
Line 27, delete "Florescence" and insert -- Fluorescence --.
Line 28, delete "Spektroskopii" and insert -- Spektroskopii, --.
Line 38, delete "Productions" and insert -- Production --.
Line 41, delete ""Acosutic" and insert -- "Acoustic --.
Line 54, delete "Phsophors" and insert -- Phosphorus --.
Line 55, delete "Irnmunocytochernistry" and insert -- Immunocytochemistry --.
Line 67, delete "ona New Eurpium" and insert -- on a New Europium --.
Line 70, delete "Microbioloaical" and insert -- Microbiological --.
Line 73, delete "microlalgae"," and insert -- microalgae", --.

Page 4, Column 1:
Line 21, delete "W.T. et al.," and insert -- W.T. --.
Line 22, delete "Tibtech," and insert -- Trends Biotechnol., --.
Line 32, delete "25,192-1 93." and insert -- 25,192-193. --.
Line 42, delete "143-1 53." and insert -- 143-153. --.
Line 43, delete "S.D. et al.," and insert -- S.D. --.
Lines 44-45, delete "Izvestiva Adademii" and insert -- Izvestiya Akademii --.
Line 49, delete "Doblhoff-Dier, 0." and insert -- Doblhoff-Dier, O. --.

Signed and Sealed this
Fifth Day of December, 2017

Joseph Matal
*Performing the Functions and Duties of the*
*Under Secretary of Commerce for Intellectual Property and*
*Director of the United States Patent and Trademark Office*

Page 4, Column 2:
Line 6, delete ""Hydronamic" and insert -- "Hydrodynamic --.
Line 15, delete "1005," and insert -- 2005, --.
Line 27, delete "31,1461-1 468." and insert -- 31,1461-1468. --.
Line 31, delete "aprticles" and insert -- particles --.
Line 39, delete "and" and insert -- und --.
Line 41, delete "Phvsik, Technishchen" and insert -- Physik, Technischen --.
Line 48, delete "performace" and insert -- performance --.
Line 49, delete "Ena." and insert -- Eng. --.
Line 70, delete "Touauet," and insert -- Touquet, --.

Page 5, Column 1:
Line 6, delete "reaquirements" and insert -- requirements --.
Line 21, delete "Unltrsound" and insert -- Ultrasound --.
Line 26, delete "combinin" and insert -- combining --.
Line 30, delete "standind" and insert -- standing --.
Line 39, delete "Fluoresncence," and insert -- Fluorescence, --.

Page 5, Column 2:
Line 4, delete "Analvsis," and insert -- Analysis, --.
Line 8, delete "blodd"," and insert -- blood", --.
Line 20, delete "1-1 3." and insert -- 1-13. --.
Line 37, delete "Svmp." and insert -- Symp. --.
Line 48, delete "and" and insert -- und. --.
Line 50, delete "buble-driven" and insert -- bubble-driven --.
Line 51, delete "a ultrasound" and insert -- an ultrasound --.
Line 61, delete "Analyical" and insert -- Analytical --.
Line 68, delete "Wied." and insert -- Wied --.

Page 6, Column 1:
Line 9, delete "Leikaemic Lymphoctyes" and insert -- Leukaemic Lymphocytes --.
Line 56, delete "Chemical ," and insert -- Chemical, --.
Line 57, delete "Neild, A.," and insert -- Neild, A., et al. --.
Line 58, delete "ultrasound" and insert -- ultrasonic --.
Line 58, delete "Micromechanical" and insert -- Micromechanics --.
Line 65, delete "fro" and insert -- for --.

Page 6, Column 2:
Line 17, delete "F.," and insert -- F., et al. --.
Line 25, delete "Ca2+Signalling" and insert -- Ca2+ Signalling --.
Line 27, delete "Aggregattion" and insert -- Aggregation --.
Line 32, delete "Surfacant" and insert -- Surfactant --.
Line 34, delete "Nouel" and insert -- Nozzle --.
Line 39, delete "F .et al.," and insert -- F. --.
Line 64, delete "Gynecolony," and insert -- Gynecology --.
Line 66, delete "Scaning" and insert -- Scanning --.

Page 7, Column 1:
Line 9, delete ""Die Grundlagen der Akustic", Sprinaer Verlaa." and insert
-- "Die Grundlagen der Akustik", Spriger Verlag. --.
Line 16, delete "2001," and insert -- 2000, --.
Line 25, delete "Cyometry," and insert -- Cytometry, --.
Line 54, delete "Trihn," and insert -- Trinh, --.

Page 7, Column 2:
Line 27, delete "Visuri, S.V. et al., "Microfluidic tolls" and insert -- Visuri, S.R. et al., "Microfluidic tools --.
Line 28, delete "Poster 1423, 2nd Annual International IEEE-EMBS" and insert -- Biology, 2nd Annual International IEEE-EMB --.
Line 29, delete "Cofnerence" and insert -- Conference --.
Lines 29-30, delete "Biology, May 2-24, 2002" and insert -- amp, May 2-4, 2002, --.
Line 50, delete "Florescent Nucleic Acid Stain" and insert -- Fluorescent Nucleic Acid Stain, --.
Line 67, delete "acousitc" and insert -- acoustic --.
Line 70, delete "paminobenzoic" and insert -- p-aminobenzoic --.

Page 8, Column 1:
Line 1, delete "Comressible" and insert -- Compressible --.
Line 4, delete "Chrnistry," and insert -- Chemistry, --.
Line 7, delete "blook" and insert -- blood --.

In the Claims

Column 5:
Claim 1, Line 52, delete "chamber," and insert -- chamber; --.

Column 6:
Claim 8, Line 23, delete "a fluid," and insert -- the fluid, --.
Claim 8, Line 30, delete "a the first" and insert -- the first --.
Claim 14, Line 56, delete "a flow path" and insert -- the flow path --.
Claim 14, Line 62, delete "and" and insert the same at Line 61, after "operation; as a continuation sub-point".